United States Patent [19]

Verdicchio et al.

[11] E Re. 30,641

[45] Reissued Jun. 9, 1981

[54] LOW IRRITATING DETERGENT COMPOSITIONS

[75] Inventors: Robert J. Verdicchio, Succasunna, N.J.; Maria C. Rodon, New Rochelle, N.Y.

[73] Assignee: Johnson & Johnson, New Brunswick, N.J.

[21] Appl. No.: 146,982

[22] Filed: May 5, 1980

Related U.S. Patent Documents

Reissue of:

[64] Patent No.: 4,186,113
Issued: Jan. 29, 1980
Appl. No.: 892,803
Filed: Apr. 3, 1978

[51] Int. Cl.[3] ..... C11D 1/92; C11D 1/94

[52] U.S. Cl. ..... 252/526; 252/529; 252/545; 252/548; 252/DIG. 13; 252/DIG. 14

[58] Field of Search ..... 252/526, 529, 545, 548, 252/DIG. 13, DIG. 14

[56] References Cited

U.S. PATENT DOCUMENTS

| | | | |
|---|---|---|---|
| 3,842,847 | 10/1974 | Hewitt et al. | 252/545 |
| 3,928,251 | 12/1975 | Bolich et al. | 252/526 |
| 4,080,310 | 3/1978 | Ng et al. | 252/548 |

*Primary Examiner*—Mayer Weinblatt
*Attorney, Agent, or Firm*—Steven P. Berman

[57] ABSTRACT

A liquid detergent composition exhibiting good cleansing characteristics and low ocular and skin irritancy comprising as the active ingredients a binary mixture of a sulfobetaine and an anionic detergent.

7 Claims, No Drawings

LOW IRRITATING DETERGENT COMPOSITIONS

Matter enclosed in heavy brackets [ ] appears in the original patent but forms no part of this reissue specification; matter printed in italics indicates the additions made by reissue.

BACKGROUND OF THE INVENTION

The present invention relates to novel detergent compositions. In particular, it relates to liquid detergent compositions which exhibit relatively low ocular and skin irritation and yet exhibit high foam volume and improved foam stability resulting in good cleansing characteristics.

Detergent compositions, like most types of liquid cleaning agents, generally comprise a mixture of one or more surfactants as the active ingredient, perfumes, coloring agents, thickeners, and the like. The surfactants normally used in such compositions have two portions: (1) a hydrophobic hydrocarbon chain miscible with organic materials and (2) a hydrophilic end-group miscible with water. When such a surfactant contacts a particle of soil, the hydrocarbon chains mix therewith and the hydrophilic end-groups are presented to the aqueous solution. This process of emulsification allows the soil, which otherwise would resist removal by the water, to be cleaned from the body thereby. These surfactants may be classified as anionic, cationic, nonionic, or amphoteric, depending upon the character of the end-groups.

It is highly desirable that liquid detergent compositions exhibit high foam volume and stability which result in good cleansing characteristics. Often, however, when compositions with such characteristics are formulated, they are not mild and result in a high incidence of ocular and skin irritation which are undesirable, particularly when utilized by children. Other desirable characteristics of liquid detergent compositions are good "slip" and easy rinsability. "Slip" can be defined as the ability to easily spread over the area desired to be cleansed.

Attempts to achieve compositions with such desirable characteristics are well documented in the art, see e.g., U.S. Pat. Nos. 3,055,836; 3,280,179; 2,999,069; 3,928,251 and the like, but these attempts have usually failed to achieve the desired results. When good cleansing compositions were formulated, they tended to result in high ocular and skin irritation and when such compositions exhibited low ocular and skin irritation they tended not to be good cleansing compositions.

SUMMARY OF THE INVENTION

It is an object of the present invention to provide improved detergent compositions.

It is another object of this invention to provide liquid detergent compositions with good cleansing characteristics.

It is a further object of this invention to provide liquid detergent compositions which exhibit good cleansing characteristics and low ocular and skin irritancy.

Other objects of this invention will be set forth in, or be apparent from, the following detailed description of the invention.

The foregoing objects and other features and advantages of the present invention are achieved by a detergent composition containing as the active ingredients a binary mixture of surfactants. More specifically, the present invention relates to a liquid detergent composition containing a binary mixture of a sulfobetaine and an anionic detergent as the active ingredients. The use of a mixture of these surfactants as the active ingredients in the liquid detergent compositions of the present invention yields compositions with good cleansing characteristics and unexpected low ocular and skin irritancy characteristics.

It has unexpectedly been found that the mixture of an anionic surfactant and a sulfobetaine at use levels which provide good cleansing characteristics result in lower ocular and skin irritation than if either of the surfactants were utilized alone at such levels to provide the cleansing characteristics. When the sulfobetaine or anionic surfactant are utilized alone at levels to produce satisfactory cleansing, the ocular and skin irritancy is undesirable whereas when a mixture of said surfactants are utilized at specific levels, the ocular and skin irritancy are significantly lower and within very acceptable levels even for use by children.

DESCRIPTION OF PREFERRED EMBODIMENTS

A preferred embodiment of the present invention comprises a liquid detergent composition containing a binary mixture of a sulfobetaine and a specific anionic detergent as the active ingredients.

The sulfobetaines useful in the present invention are of the formula:

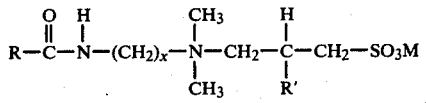

wherein R is an alkyl group of from 8 to 18 carbon atoms or mixtures thereof; R′ is OH or H; x is an integer from 1 to 3; and M is selected from alkali metals such as lithium, sodium or potassium, akaline earth metals such as magnesium and calcium, and alkanol amine salts such as the mono-, di-, or triethanolamine salts.

A preferred sulfobetaine is one of the formula:

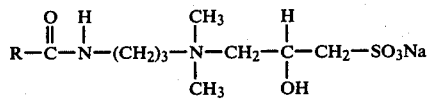

wherein R is an alkyl group containing 12 carbon atoms or a mixture of alkyl groups containing from 12 to 18 carbon atoms.

The sulfobetaine comprises about 1–15% by weight of the total composition, preferably about 2–6% by weight, provided, however, that the total amount of sulfobetaine and anionic surfactant is not greater than about 20% by weight of the detergent composition. If less than about 1% by weight of the sulfobetaine is utilized, the resulting detergent composition will not foam and clean satisfactorily; and if greater than about 15% of the sulfobetaine is utilized, eye irritation is undesirably increased and such is also economically unfeasible.

The anionic detergents useful in the present invention are the alkyl ether sulfates of the formula:

$$R''—O—(C_2H_4O)_x—SO_3—M$$

wherein R″ is a branched or straight chain saturated or unsaturated aliphatic hydrocarbon radical, alkylaromatic hydrocarbon radical or alkylaryl hydrocarbon radical having from 6 to 20 carbon atoms; x is an integer from 1–5 and M is selected from alkali metals such as lithium, sodium or potassium; alkaline earth metals such as magnesium and calcium, and alkanolamine salts such as the mono-, di-, or triethanolamine salts.

A preferred anionic detergent is one of the formula:

$$R''—O—(C_2H_4O)_4—SO_3Na$$

wherein R″ is a branched chain aliphatic hydrocarbon radical having 13 carbon atoms.

The anionic detergent comprises about 1–15% by weight of the total composition, preferably about 2–6% by weight, provided, however, that the total amount of anionic surfactant and sulfobetaine is not greater than about 20% by weight of the detergent composition. If less than about 1% by weight of the anionic surfactant is utilized, the resulting detergent composition will not foam or clean satisfactorily; and if greater than about 15% is utilized, eye and skin irritation is undesirably increased.

To achieve the desired results of this invention, the sulfobetaine should be utilized in a weight ratio of 3:1 to 1:3 to the anionic detergent, preferably in a weight ratio of about 1:1.

Thus, the liquid detergent composition of the invention comprises from about 1% to about 15% by weight of sulfobetaine and from about 1% to about 15% by weight of anionic surfactant based upon the weight of the entire composition, but the total of the active ingredients is not greater than 20% by weight of the entire composition. The remainder of the composition is essentially water, but it may also contain thickeners, dyes, perfumes, antibacterial agents, preservatives, pH adjusters, and the like, as desired. The preferred compositions of the invention comprise about 2% to about 6% by weight of sulfobetaine and from about 2% to about 6% by weight of anionic surfactant based on the weight of the entire composition.

The liquid detergent compositions of the invention are prepared by mixing the sulfobetaine and the anionic surfactant together with a small amount of deionized water, preferably at ambient temperature, to form a mixture, and a thickener (if desired) is mixed in. Elevated temperatures may be employed at this stage to promote easier mixing of the ingredients. Then additional deionized water is mixed in to bring the weight of the composition to about three-quarters of its final weight, and the pH is adjusted to from about 5.0 to 8.0, preferably about 6.5–7.0 by addition of a mineral acid (e.g., hydrochloric acid) or a solution of a strong base (e.g., sodium hydroxide). Finally, the remainder of the deionized water is added and the pH is again adjusted within the desired range. Other ingredients such as preservatives, dyes, perfumes, skin conditioning agents, emollients, and the like may be added in any of the last three steps.

Specific embodiments of the present invention are illustrated by the following examples. It will be understood, however, that the invention is not confined to the specific limitations set forth in the individual examples, but rather to the scope of the appended claims. All parts are by weight unless indicated otherwise.

EXAMPLE I

A liquid detergent cleansing composition is prepared by charging 500 lbs. of deionized water to a stream jacketed vessel and 0.5 lbs. of a [thickener] *chelating agent*, Versene 100 with agitation. 111.0 lbs. of a 44% active solution of a sulfobetaine of the formula:

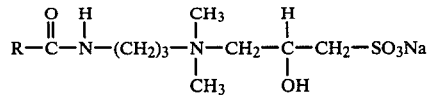

wherein R is a mixture of alkyl groups containing from 12 to 18 carbon atoms, and 156.3 lbs. of a 32% active solution of a alkyl ether sulfate of the formula:

$$R''—O—(C_2H_4O)_4—SO_3Na$$

wherein R″ is a branched chain aliphatic hydrocarbon radical having 13 carbon atoms, are then added and the resulting mixture is then heated to 50°–60° C. 15.0 lbs. of a thickener, polyethylene glycol distearate are added and agitation is provided until the mixture is clear and then [128.0] *5.00* lbs. of an emollient, Arlamol E, are added [followed by the addition of 211.75 lbs. of deionized water]. The mixture is then cooled to 40° C. and 1.0 lb. of a preservative, Dowicil 200, 3 lbs. of benzyl alcohol, 0.75 lbs. of fragrance are added followed by the addition of 5.0 lbs. of phosphoric acid and 20 lbs. of a phosphate buffer solution to adjust the pH to about 6.8 *and sufficient deionized water is added to bring the total change to 1000 lbs.* The resulting solution is cooled with agitation to room temperature and consists of the following ingredients:

| | % |
|---|---|
| [32% active solution] alkyl ether sulfate | [4.06] *5.00* |
| Ariamol E ICI/Americas Inc. tradename for polyoxyporpylene (15) stearyl ether | [12.8] *0.50* |
| [44% active solution] sulfobetaine | 4.88 |
| phosphate buffer | 2.0 |
| polyethylene glycol 6000 distearate | 1.5 |
| fragrance | 0.075 |
| Versene 100 Dow Chemical Company's tradename for ethylene diamine tetrasodium acetate | 0.05 |
| phosphoric acid | [0.05] *0.50* |
| benzyl alcohol | [0.03] *0.30* |
| Dowicil 200 Dow Chemical Company's tradename for the cis isomer of 1-(3-chloroalkyl)-3,5,7-triaza-1-azoneaadamantine chloride | [0.01] *0.10* |
| deionized water | q.s to 100% |

The liquid detergent cleansing composition of this example is tested for ocular irritation by the following modified Draize test (see J. H. Draize et al., Toilet Goods Associations #17, May, 1952, #1 Proc. Sci. Sect.):

A 1 ml. sample of the neutral composition under test is dropped into one eye of each of six rabbits. Daily administration of the same quantity of each of the samples is continued for 3 consecutive days. Observations are recorded after one hour, one day, two days, three days, four days and seven days after samples are dropped into the eyes. The extremes of the results either show substantially no change or show only a slight irritation (foreign body effect) in the appearance of the rabbit's eyes after seven days, or severe irritation or complete corneal opacity, as the case may be.

The composition prepared in Example I is tested by this procedure and found to be only a very slight irritant a.

The liquid detergent cleansing composition of this example is tested for foam volume and stability as measured by the following modification of the well-known Ross-Miles foam test ["Oil and Soap", 18, 99-102 (1941)]:

Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45° C. in order to dissolve the lanolin in the dioxane. The remainder of the dioxane is then added and mixed. This lanolin-dioxane solution, which is stored in an amber bottle, should be prepared fresh on the day that the tests are run.

The composition to be tested is diluted by adding 376 cc. of distilled water to 4 grams of the composition, and then by adding 20 cc. of the lanolin-dioxane solution described above while mixing. Heat is produced when the lanolin-dioxane solution is added to the solution of the composition in water and care must be taken in adjusting the temperature of this solution to 24°-25° C. Both of these intermediate solutions should therefore be adjusted to 23° C. before mixing. The cooling of the lanolin-dioxane solution should be gradual in order to avoid precipitation of the lanolin. This will produce a final solution with a temperature of 24°-25° C.

The final solution of the composition to be tested, water, dioxane and lanolin described above, is then run in a modified Ross-Miles foam column in the usual way. All tests are conducted in duplicate, and the average of the two results is taken. Foam stability is determined by measuring the decay in foam height after five minutes, expressed as a percentage of the original height.

The detergent composition of this example possesses a high foam volume and significantly superior foam stability when compared to a leading commercial personal cleansing product as demonstrated by the following results:

| | Foam Volume (MM) | % Decay |
|---|---|---|
| Composition of Example I | 180 | 17.0 |
| Commercial Product | 175 | 85.0 |

EXAMPLES II-V

Liquid detergent cleansing compositions consisting of the following ingredients are prepared in accordance with the procedure of Example I:

| | % W/W Example | | | |
|---|---|---|---|---|
| | II | III | IV | V |
| sulfobetaine of Example I | 4.950 | 1.000 | 5.000 | 15.000 |
| alkyl ether sulfate of Example I | 4.096 | 1.000 | 15.000 | 5.000 |
| phosphate buffer | 2.000 | 2.000 | 2.000 | 2.000 |
| deionized water | q.s. to 100 | q.s. to 100 | q.s. to 100 | q.s. to 100 |

These compositions all exhibit low ocular and skin irritation and excellent foam stability.

EXAMPLES VI-VII

Liquid detergent cleansing compositions consisting of the following ingredients are prepared in accordance with the procedure in Example I:

| | % W/W Example | |
|---|---|---|
| | VI | VII |
| sulfobetaine of Example I | 9.046 | — |
| alkyl ether sulfate of Example I | — | 9.046 |
| phosphate buffer | 2.000 | 2.000 |
| deionized water | q.s. to 100 | q.s. to 100 |

The compositions of Examples II, VI and VII are tested for eye irritation by means of the modified Draize test described in Example I above and the results are reported in Table 1 below:

TABLE 1

| Composition | Eye Irritancy Score |
|---|---|
| Example II | 11.3 |
| Example VI | 47.0 |
| Example VII | 12.0 |

As can be readily seen from the results in Table 1, the composition of Example II containing the sulfobetaine and alkyl ether sulfate demonstrated an unexpected lower eye irritancy score than either the composition of Example VI (sulfobetaine alone) or Example VII (alkyl ether sulfate alone) even though the total concentration of active surfactant ingredients in each of the compositions is about the same. This demonstrates a synergistic reduction in eye irritancy with the combination of surfactants of the compositions of the present invention as well as providing good cleansing characteristics.

In addition to the preferred embodiments described herein, other embodiments, arrangements and variations within the spirit of the invention and the scope of the appended claims will occur to those skilled in the art.

What is claimed is:

1. A low irritating liquid detergent composition wherein the active ingredients consist essentially of:

(a) from about 1 to 15% by weight of the total composition of a sulfobetaine of the formula

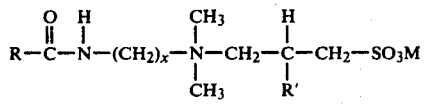

wherein R is an alkyl group of from 8 to 18 carbon atoms or mixtures thereof, R′ is OH or H, x is an integer from 1 to 3 and M is selected from the group consisting of alkali metals, alkaline earth metals and alkanol amine salts selected from the group consisting of mono-, di- and triethanolamine salts; and (b) from about 1 to 15% by weight of the total composition of an anionic detergent of the formula $$R''—O—(C_2H_4O)_x—SO_3M$$

wherein R'' is a branched or straight chain saturated or unsaturated hydrocarbon radical, alkylaromatic hydrocarbon radical or alkylaryl hydrocarbon radical containing from 6 to 20 carbon atoms, x is an integer from 1 to 5 and M is selected from the group consisting of alkali metals, alkaline earth metals and alkanol amine salts;

wherein the total of (a) and (b) does not exceed about 20% by weight of the total composition.

2. The composition of claim 1 wherein the anionic detergent is present in an amount of from about 2 to 6% by weight of the total composition.

3. The composition of claim 1 wherein the sulfobetaine is present in an amount of from about 2 to 6% by weight of the total composition.

4. The composition of claim 1 wherein the anionic detergent is of the formula $$R''—O—(C_2H_4O)_4—SO_3Na$$

wherein R'' is a branched chain aliphatic hydrocarbon radical containing 13 carbon atoms.

5. The composition of claim 1 wherein the sulfobetaine is of the formula

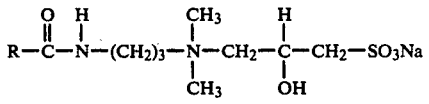

wherein R is an alkyl group containing 12 carbon atoms or a mixture of alkyl groups containing from 12 to 18 carbon atoms.

6. The composition of claim 2 wherein the sulfobetaine and anionic detergent are present in a weight ratio of about 1:1.

7. The composition of claim 1 wherein the sulfobetaine and anionic detergent are present in a weight ratio of from about 3:1 to about 1:3.

* * * * *